(12) United States Patent
Ishimaru et al.

(10) Patent No.: US 8,253,097 B2
(45) Date of Patent: Aug. 28, 2012

(54) MASS SPECTROMETER AND METHOD OF MASS SPECTROMETRY

(75) Inventors: Masako Ishimaru, Tokyo (JP); Masuyoshi Yamada, Ichikawa (JP)

(73) Assignee: Hitachi, Ltd., Tokyo (JP)

( * ) Notice: Subject to any disclaimer, the term of this patent is extended or adjusted under 35 U.S.C. 154(b) by 478 days.

(21) Appl. No.: 12/039,762

(22) Filed: Feb. 29, 2008

(65) Prior Publication Data

US 2009/0039250 A1 Feb. 12, 2009

(30) Foreign Application Priority Data

Aug. 6, 2007 (JP) ................................. 2007-203764

(51) Int. Cl.
*H01J 49/00* (2006.01)
(52) U.S. Cl. ......................... 250/288; 250/290; 250/292
(58) Field of Classification Search ................... 250/288
See application file for complete search history.

(56) References Cited

U.S. PATENT DOCUMENTS

| | | | | |
|---|---|---|---|---|
| 5,338,514 | A * | 8/1994 | Morabito et al. | 422/89 |
| 5,739,422 | A * | 4/1998 | Riviello et al. | 73/61.55 |
| 2005/0194543 | A1* | 9/2005 | Hieke | 250/400 |
| 2007/0029477 | A1* | 2/2007 | Miller et al. | 250/290 |
| 2007/0181801 | A1 | 8/2007 | Yamada et al. | |

FOREIGN PATENT DOCUMENTS

| | | |
|---|---|---|
| JP | 9-15207 | 1/1997 |
| JP | 11-307041 | 11/1999 |
| JP | 2003-357488 | 12/2000 |
| JP | 2003-254955 | 9/2003 |

OTHER PUBLICATIONS

Jenny A. Turner et al., Real-Time Monitoring of Thermal Flavor Generation in Skim Milk Powder Using Atmospheric Pressure Chemical Ionization Mass Spectrometry, Journal of Agricultural and Food Chemistry, (2002), 50, 5400-5405.
A. Good, et al., Ion-Molecule Reactions in Pure Nitrogen and Nitrogen Containing Traces of Water at Total Pressures 0.5-4 torr. Kinetics of Clustering Reactions Forming H+(H2O)n, Journal of Chemical Physics, vol. 52, No. 1 (Jan. 1, 1970) pp. 212-221.

* cited by examiner

*Primary Examiner* — Phillip A Johnston
(74) *Attorney, Agent, or Firm* — Antonelli, Terry, Stout & Kraus, LLP.

(57) ABSTRACT

In a mass spectrometer having ion sources capable of switching between atmospheric pressure chemical ionization and electron impact ionization, a first gas chromatography device capable of separating a sample to meet a condition suitable for atmospheric pressure chemical ionization measurement is connected to upstream of an atmospheric pressure chemical ionization ion source. Part of the sample separated by the first gas chromatography device is introduced to a second gas chromatography device by distributing a flow channel. In the second gas chromatography device, a target substance and background ingredients contained in the sample are further separated and are introduced to an electron impact ionization ion source. By separating the target substance from the background ingredients, an electron impact ionization spectrum of the target substance is obtained without an effect of the background ingredients.

27 Claims, 8 Drawing Sheets

MASS SPECTROMETER AND METHOD OF MASS SPECTROMETRY

CLAIM OF PRIORITY

The present application claims priority from Japanese application JP 2007-203764 filed on Aug. 6, 2007, the content of which is hereby incorporated by reference into this application.

BACKGROUND OF THE INVENTION

1. Field of the Invention

The present invention relates to a mass spectrometer for analyzing a sample gas separated by gas chromatography and to a method of analysis using the same.

2. Description of the Related Art

In the following description, gas chromatography will be abbreviated as GC, liquid chromatography will be abbreviated as LC, a mass spectrometer will be abbreviated as MS, an apparatus in which gas chromatography and a mass spectrometer are combined will be abbreviated as GC/MS (gas chromatography/mass spectrometer), atmospheric pressure chemical ionization will be abbreviated as APCI, chemical ionization will be abbreviated as CI, electron impact ionization will be abbreviated as EI, and electro-spray ionization will be abbreviated as ESI.

Many studies for an attempt to use a mass spectrometer for diagnoses of diseases are in progress in recent years. In particular, a mass spectrometer is frequently used in order to search for a disease marker.

In a search for a disease marker, specimens are acquired respectively from a healthy person and from a patient of a specific disease, and then metabolites and proteins contained in the specimens are comprehensively analyzed with a mass spectrometer to find out a substance that differentiates between the healthy person and the patient. Gas samples such as breath or urine headspace gas, liquid samples such as blood, urine, saliva or tear, cells, and tissues are used as the specimens for searching for the disease marker. Numerous specimens must be measured in order to ensure reliability of the disease marker. Moreover, it is necessary to discover a small number of substances that differentiate between the healthy person and the patient among an extremely large number of substances contained in these specimens. Further, it is essential to identify the substance discovered as the disease marker so as to consider a relation between the disease marker and a mechanism of the development of the disease. In order to perform this operation efficiently, it is effective to use a combination of GC/APCI/MS and GC/EI/MS in the case of a gas sample or a combination of LC/APCI (or ESI)/MS and LC/EI/MS in the case of a liquid sample.

The APCI/MS is an apparatus for ionizing micro-amount of ingredients in a mixed sample by using ion-molecular reaction, and for thus detecting the ionized ingredients with high sensitivity, and is used for the analysis of micro-ingredients in environmental samples or biological samples. The APCI is a soft ionization method with which molecules hardly break down at the time of ionization. Accordingly, it is possible to measure a molecular weight of the molecules and also to measure individual molecular weights even when multiple substances enter an ion source to be ionized at the same time. Since several thousand types of substances are contained in the specimen, it is practically necessary to conduct separation of substances by the GC prior to ionization. However, as it is possible to detect multiple substances at the same time, it is only necessary to conduct rough separation for a short time period. For this reason, the APCI/MS is effective for measuring and comparing numerous specimens and for discovering different substances therein. Japanese Patent Application Publication No. Hei 9-15207 discloses an analyzer with high sensitivity in which GC and APCI/MS are combined for conducting analysis of various kinds of micro-impurities including special gases for use in semiconductor manufacturing. In the apparatus, a sample gas separated in the GC column is introduced in admixture with a carrier gas through a line to an APCI source and analyzed.

Meanwhile, the EI/MS is a mass spectrometer using a high energy ionization method in which a thermoelectron is caused to collide with a molecule. The EI/MS is capable of identifying a substance from a pattern of fragment ions generated by a breakup of a molecule at the time of ionization. As an example of combining the APCI/MS with the EI/MS, Non-patent Document 1 discloses the following method. In this method, substances are distributed at a tee after separation by GC, and then introduced to the APCI/MS and to the EI/MS, so that measurement is performed in the two MS at the same time.

Meanwhile, as an example of installing two types of ion sources onto one MS, Japanese Patent Application Publication No. Hei 11-307041 discloses an apparatus in which a first ionization chamber for CI, a second ionization chamber for EI, and a mass spectrometer part are serially in adjacent to with each other, and a passage port for passing ions is disposed between each of the ion sources. The sample gas enters the first ionization chamber and is introduced into the second ionization chamber through the passage port. The sample gas is ionized in a state of stopping an EI operation at the time of a CI operation while the sample gas is ionized in a state of stopping the CI operation at the time of the EI operation, thereby analyzing the introduced sample while switching the two ion sources.

Japanese Patent Application Publication No. 2000-357488 discloses an apparatus of separating ingredients flown out of a single LC by use of branch tee and to send the ingredients to two ion sources for the ESI and the APCI. It is possible to perform analyses in accordance with two ionization methods by switching the ion sources.

Meanwhile, as a method of separating a mixed sample at high degree, Patent Document 4 discloses an apparatus using two LC that apply different separation methods. A sample separated by the first LC is measured with a UV-visible spectrometer and absorbed separately by multiple trap columns, and is further separated by the second LC and measured with a mass spectrometer. In this way, the degree of separation of the sample containing various substances is improved.

[Patent Document 1] Japanese Patent Application Publication No. Hei 9-15207

[Patent Document 2] Japanese Patent Application Publication No. Hei 11-307041

[Patent Document 3] Japanese Patent Application Publication No. 2000-357488

[Patent Document 4] Japanese Patent Application Publication No. 2003-254955

[Non-patent Document 5] Journal of Agricultural and Food Chemistry (2002) p. 5400-5405

SUMMARY OF THE INVENTION

Although the method of combining the APCI/MS and the EI/MS is effective for searching for a disease marker out of a gas sample using the MS, this method has a problem of a high apparatus cost because the two MS are required.

The EI/MS is able to identify a substance by use of a pattern of fragment ions generated by a breakup of a molecule at the time of ionization and to identify the substance by performing database search because EI/MS spectra for more than ten thousand types of substances have already been stored in a database. However, since numerous fragments are generated in EI ionization, multiple fragment ions are observed from a single substance in the case of an EI/MS spectrum. For this reason, when multiple substances are ionized at the same time, spectra will be complicated and identification accuracy is degraded. It causes difficulty particularly in identifying a small number of target substances existing in a large variety of background ingredients.

A mass spectrometer according to the present invention includes a first sample ion source and a second ion source for performing ionization of a sample which are disposed adjacently to each other, and a mass spectrometry unit located on downstream of the second sample ion source.

A sample introduced to a first separator is separated in accordance with a column condition and the like in the first separator. The sample separated in the first separator is distributed at a tee. A part of the separated sample is introduced to the first sample ion source while the other part thereof is sent to a second separator. The sample sent to the second separator is further separated in accordance with a column condition and the like in the second separator and is introduced to the second sample ion source.

In addition, a delay channel is provided between the tee and the second separator. For example, a silica capillary or the like having an inactive inner surface is cut off into an appropriate length for generating a required delay time period and is used as the delay channel. The delay time period is set so that a time period required for the sample separated by the first separator to pass through the delay channel through the tee becomes longer than a time period required for the sample to be ionized by the first sample ion source and then detected. This makes it possible to switch a valve provided on the upstream of the second separator after a target substance is detected from the sample ionized by the first sample ion source. Accordingly, the sample containing the target substance can be sent to the second separator without being exhausted.

Moreover, a mechanism for sending the sample separated in the first separator to a trap column is provided between the delay channel and the second separator. By controlling capture and detachment of the sample with the trap column, it is possible to introduce a larger amount of the sample to the second sample ion source. Particularly in the case of identifying, by use of the EI/MS, a substance contained only in a very small amount, identification accuracy is improved due to enhancement of ion intensity.

According to the present invention, it is possible to achieve ionization using two types of ion sources with a single MS, and to improve accuracy of identifying a substance.

DETAILED DESCRIPTION OF THE PREFERRED EMBODIMENTS

[First Embodiment]

Figure 1:
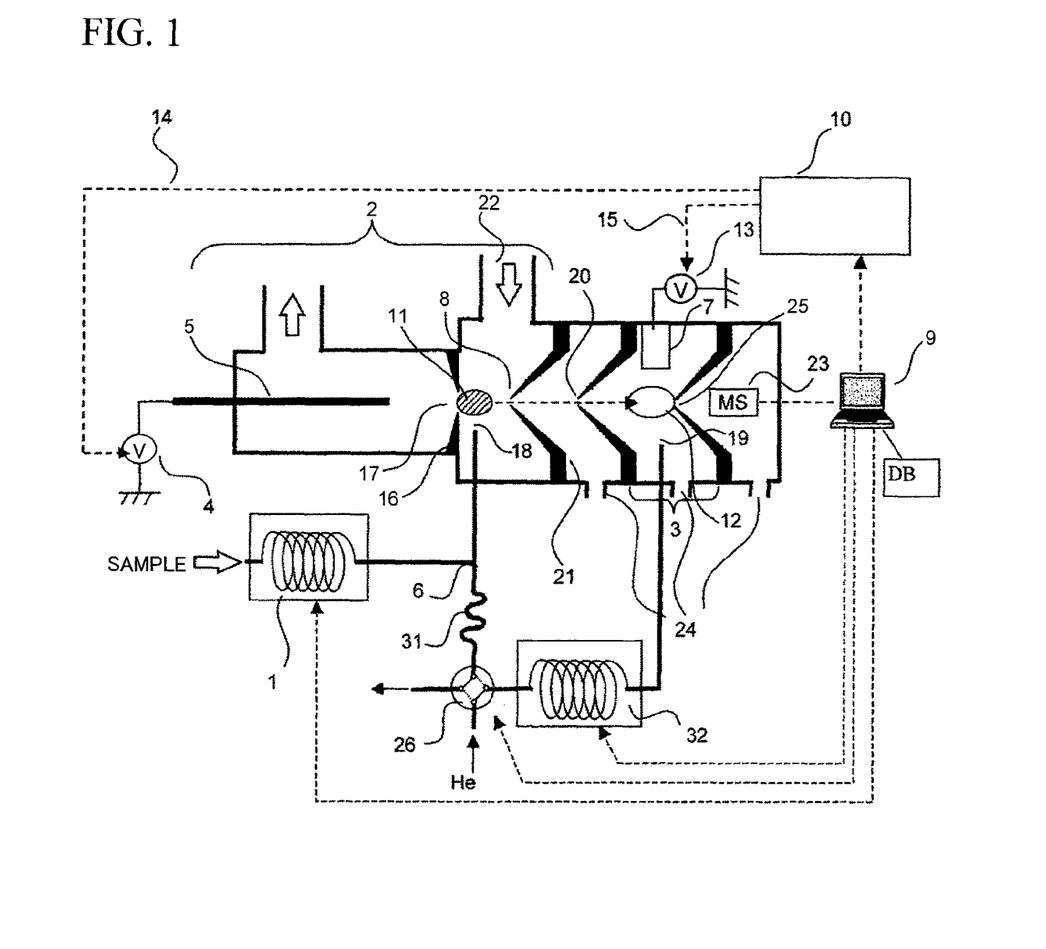
FIG. 1 is a schematic diagram showing a configuration example of a mass spectrometer according to the present invention.

FIG. 1 shows an apparatus configuration example of a mass spectrometry system based on the present invention.

As for ion sources, it is possible to use a combination of a high pressure ion source and a low pressure ion source. Such combinations include APCI and EI, ESI and EI, CI and EI, APCI and CI, and ESI and CI, for example. It is also possible to combine other ion sources applying different ionization methods. Meanwhile, it is possible to use GC and LC as a separating means. Here, a case of using an APCI ion source and an EI ion source while using GC as the means for separating a sample will be described.

An APCI ion source 2 and an EI ion source 3 are disposed adjacently to each other and a mass spectrometry unit 23 is located on downstream of the EI ion source. A first GC 1 and a second GC 32 are provided in the apparatus. A sample introduced to the first GC 1 is separated in accordance with, by the first GC 1, a column condition, a carrier gas flow rate, and a temperature condition. A sample gas flowing through the GC column 1 is distributed at a tee 6. A part of the separated sample gas is introduced to the APCI ion source 2 and the other part thereof is sent to a switching valve 26. The switching valve 26 can make selection of either discharging the fed gas or sending the gas to the second GC 32. When the sample is sent to the second GC 32, the sample is separated in accordance with, by the second GC 32, a column condition, a carrier gas flow rate, and a temperature condition and is introduced to the EI ion source 3. The first GC, the second GC, the valve 26, and a controller for the ion sources are controlled by a computer 9.

The APCI ion source 2 and an EI ion source 3 are separated by a differential vacuum pumping region 21 provided with an aperture 8 and an aperture 20. The differential vacuum pumping region 21 and the EI ion source 3 are exhausted by a vacuum pump from exhaust ports 24. The APCI ion source 2 may adopt corona discharge using a needle electrode 5 as shown in FIG. 1, or may adopt a radiation source.

Now, a case of adopting the corona discharge will be described below. For stably maintaining discharge, discharge gas (such as air) is introduced at about 0.5 to 1.0 L/min to the APCI ion source 2. In FIG. 1, the discharge gas flows from the forward to the top end of the needle electrode 5. Instead, the discharge gas may flow from the base to the top end of the needle electrode 5.

When dry air is used for the discharge gas, primary ions ($N_2^+$ or $N_4^+$) are generated as a consequence of a reaction expressed either in (Equation 1) or in (Equation 2) below (see The Journal of Chemical Physics, Vol. 52, 212 to 229 (1970)).

(Equation 1)

(Equation 2)

A lead-out electrode 16 is provided with a primary ion introduction aperture 17 having a diameter of about 2 mm, and the generated primary ions are introduced to an APCI ion source 11 by an electric field. In the APCI ion source 11, the primary ions generated by the corona discharge react with the sample gas introduced from an end 18 at the exit of the GC column, thereby generating ions of the sample gas. The generated sample ions are introduced to a mass spectrometer 23 through the aperture 8, the aperture 20, and an aperture 25 and analyzed.

The sample gas introduced to the APCI ion source 2 is directly introduced from the end 18 of the GC column to the APCI ion source 11 from a position near the axis connecting the center of the primary ion introduction aperture 17 through which the primary ions pass and the center of the aperture 8 through which the sample ions move.

Assuming the radius for the primary ion introduction aperture 17 as R and a distance from the axis connecting the center of the primary ion introduction aperture 17 and the center of the aperture to the center of the opening at the end of the GC column is r, the center of the opening of the end 18 of the GC column is situated at a position with a substantially equal distance from the center of the ion exit of the primary ion introduction aperture 17 and that from the center of the ion inlet of the sample ion moving aperture and capable of satisfying $r \leqq 2R$. By satisfying this condition, since the staying time in which the primary ions introduced from the primary ion introduction aperture 17 and the sample gas introduced from the end of the GC column are present together can be made longer and a sufficient time to proceed ion-molecule reaction can be ensured, high sensitivity can be obtained.

If the center of the opening 18 at the end of the GC column approaches excessively to the aperture 8, almost all the sample gas is exhausted from the sample ion moving aperture 8. Since the staying time in which the primary ions and the sample molecules are present together in the field of ion-molecule reaction is shortened and sufficient time to proceed the ion-molecule reaction can not be ensured, the amount of the generated sample ions is lowered to lower the sensitivity.

Meanwhile, if the center of the opening 18 at the end of the GC column approaches excessively to the primary ion introduction aperture 17, almost all the sample gas is exhausted from the primary ion introduction aperture 17. In this case, the sample gas is exhausted, while not being ionized, from the primary ion introduction aperture 17. Accordingly, as similar to the foregoing case, the staying time in which the primary ions and the sample molecules are present together in the field of ion-molecule reaction is shortened in the same manner, sufficient time to proceed the ion-molecule reaction and the amount of generated sample ions is decreased and the sensitivity is lowered.

That is, in order to achieve higher sensitivity, the center of the opening 18 at the end of the GC column is situated at a position between the primary ion introduction aperture 17 and the aperture 8 where the time required for exhausting the sample gas introduced from the opening 18 at the end of the GC column out of the primary ion introduction aperture 17 or the aperture 18 becomes the longest. Accordingly, the staying time where the primary ions and the sample molecules are present together in the field of the ion-molecule reaction is made sufficiently long to ensure a sufficient time to proceed the ion-molecule reaction. Hence it is possible to increase the amount of generated sample ions to improve the sensitivity.

When the flow rate of the sample gas flowing through the opening 18 at the end of the GC column is Q and a flow rate in Q which is exhausted through the aperture 8 to the differential vacuum pumping region 21 is Q', it is preferred that the center position of the opening 18 at the end of the GC column in the direction of the axis is controlled so as to satisfy: $0.02Q \leqq Q' \leqq 0.9Q$, and further, the center position of the opening 18 is controlled to a position: $r \leqq 2R$ in the vicinity of the axis indicated with a chain line where the concentration of the primary ions is high.

In the EI ion source 3, electrons emitted from an electron generation device (a filament 7) provided inside the ion source collide against the sample molecules that are introduced from the end 19 at the exit of the other GC column to cause ionization. It is also preferable to situate the end 19 at the exit of the GC column in the vicinity of an axis connecting the aperture 20 and the aperture 25.

Switching between the APCI and EI ion sources is conducted by signals from a controller 10. When performing APCI ionization, a signal 14 is transmitted to turn on a power source 4 for the needle electrode and a signal 15 is transmitted to turn off a filament power source 13 for the EI ion source. On the contrary, when performing EI ionization, the power source 4 for the needle electrode is turned off and the filament power source 13 is turned on.

Ingredients ionized by the APCI or the EI are analyzed in the mass spectrometry unit 23 and are displayed on or saved in a data collector 9 in the form of a mass spectrum. The mass spectrometer applicable thereto includes a quadrupole mass spectrometer, an ion trap mass spectrometer, an ion trap TOF (time of flight) mass spectrometer, a magnetic sector mass spectrometer, and the like.

A pressure of the APCI ion source is set substantially equal to an atmospheric pressure while a pressure of the EI ion source 3 is set to a $10^{-3}$ [torr] order. Here, it is possible to omit the differential vacuum pumping region when the aperture 8 at the first stage is sufficiently small and the pressure in the EI ion source 3 can be maintained at a $10^{-3}$ [torr] level.

Since the APCI ion source 2 is operable at the atmospheric pressure, it is possible to introduce the sample gas at a gas flow rate around 10 mL/min. Accordingly, the GC column used in the first GC 1 may adopt a wide-bore capillary column having an inside diameter of 0.53 mm, for example. In this way, it is possible to introduce a larger amount of the sample and thereby to detect micro-ingredients therein.

Since the EI ion source 3 is operated at the pressure around $10^{-3}$ torr, it is necessary to introduce the sample gas at a gas flow rate around 1 mL/min. Accordingly, a narrow-bore capillary column having an inside diameter of 0.25 mm, for example, is suitable for the GC column used in the second GC.

Accordingly, it is preferable to set the flow rate to 10 mL/min in the first GC, to adjust a ratio of the flow rates, at tee 6, to be separated between the APCI side and the second GC side to a proportion around 9 to 1, and thereby to send the sample to the APCI ion source side at a flow rate of 9 mL/min and to the second GC side at a flow rate of 1 mL/min.

A delay channel 31 is provided on the downstream side of the tee 6. A silica capillary or the like having an inactive inner surface is cut off into an appropriate length for generating a required delay time period and is used as the delay channel. For example, an inner volume of the delay channel may be set to 0.17 mL so that the sample costs 10 seconds to pass at the flow rate of 1 mL/min. In this way, even when the valve is switched after detecting a target substance with the APCI/

MS, it is possible to send the sample gas containing the target substance to the second GC without exhaust.

Figure 2:
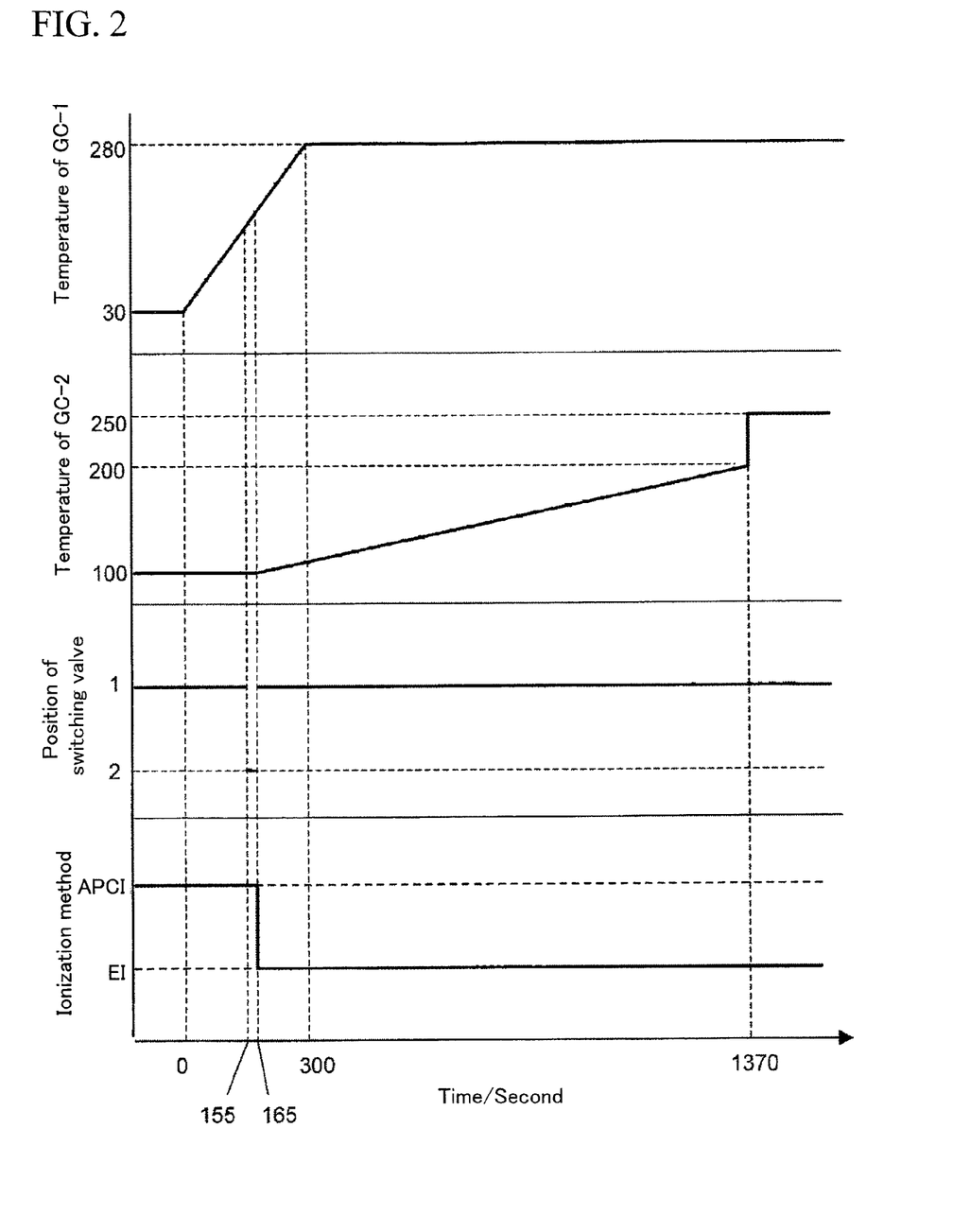
FIG. 2 is a chart showing time control of operations of respective units in measurement using the apparatus configuration shown in FIG. 1.

FIG. 2 shows an example of operations of the respective units in measurement using the apparatus configuration in FIG. 1.

Preceding the measurement using the APCI and the EI, multiple specimens are retrieved from a patient and a healthy person and all the specimens are subjected to GC/APCI/MS measurement under the same condition. A peak unique to the specimen of the patient or the healthy persons is selected by means of comparing respective measurement results. This peak is defined as a disease marker candidate and retention time of the GC and a spectrum are recorded on a computer. FIG. 2 shows an apparatus operation example for identifying a disease marker candidate peak which is detected in a retention time period of 150 seconds.

It is preferable to configure the first GC 1 to perform separation of the sample under the same condition as the method used for selecting the disease marker candidate. The substance separated by the first GC 1 is ionized by the APCI ion source 2 and detected by the MS 23. When the substance is confirmed with the computer as the target disease marker candidate based on the obtained spectrum pattern and the retention time period, the sample gas is sent to the second GC 32 by switching the switching valve 26 to a position 2.

The sample is separated by use of the first GC 1 and subjected to the APCI/MS measurement while setting the time when sample is introduced as 0 second. The switching valve 26 is switched to the position 2 when the computer 9 confirms that the spectrum matching the disease marker candidate recorded in advance at the retention time of 150 seconds within a margin of error. When the sample gas flowing for 5 seconds before and after a point of detection of the target disease marker candidate is expected to be sent to the second GC 32, a time period for allowing the sample gas to pass through the delay channel 31 and to reach the switching valve 26 may be set longer by 10 seconds than a time period for allowing the sample gas to pass through the tee 6 and then to be detected by the APCI/MS. In this way, it is possible to send the sample gas containing the target disease marker surely to the second GC 32 by switching the switching valve 26 to the position 2 for a time period counted from 155 seconds to 165 seconds.

After sending the sample gas to the second GC 32, ionization method is switched to the EI. The sample sent to the second GC 32 is separated again. The second GC 32 can separate the target disease marker candidate from other background ingredients by slowly increasing the temperature. In this way, the number of ingredients to be simultaneously introduced to the EI ion source 3 is decreased and it is possible to reduce interferences by fragment ions derived from the background ingredients. Accordingly, it is possible to improve identification accuracy by use of the EI spectrum of the target substance.

When a measurement condition in the first GC is different from a measurement condition for selecting the disease marker candidate, it is possible to calibrate retention time by analyzing a standard sample mixture for calibration of retention time with the first GC 1 and the APCI ion source 2, prior to the analysis. Instead, it is also possible to mix, with the sample, the standard sample mixture for calibration of retention time, which mixture including index substances having smaller or larger retention time than that of the disease marker candidate, and then to introduce, to the second GC 32, the sample gas having the retention time between the above-described two retention times. Here, a background ingredient essentially included in the sample may be selected in advance as the index substance. Alternatively, it is also possible to calibrate the retention time in real time with the computer 9 during the measurement by use of the retention time of the standard sample mixed with the sample or that of the background ingredient always included therein and to calculate expected retention time of the disease marker candidate.

FIG. 3 to FIG. 8 show measurement examples using the APCI/MS and the EI/MS.

For example, assuming that the number of ingredients eluted in GC temperature range from 30° C. to 280° C. is 1000 types and that an average full width at half maximum of peak on chromatography is equal to 1 second, the number of substances to be simultaneously detected in MS measurement is equal to 3 types on average.

Figure 3:
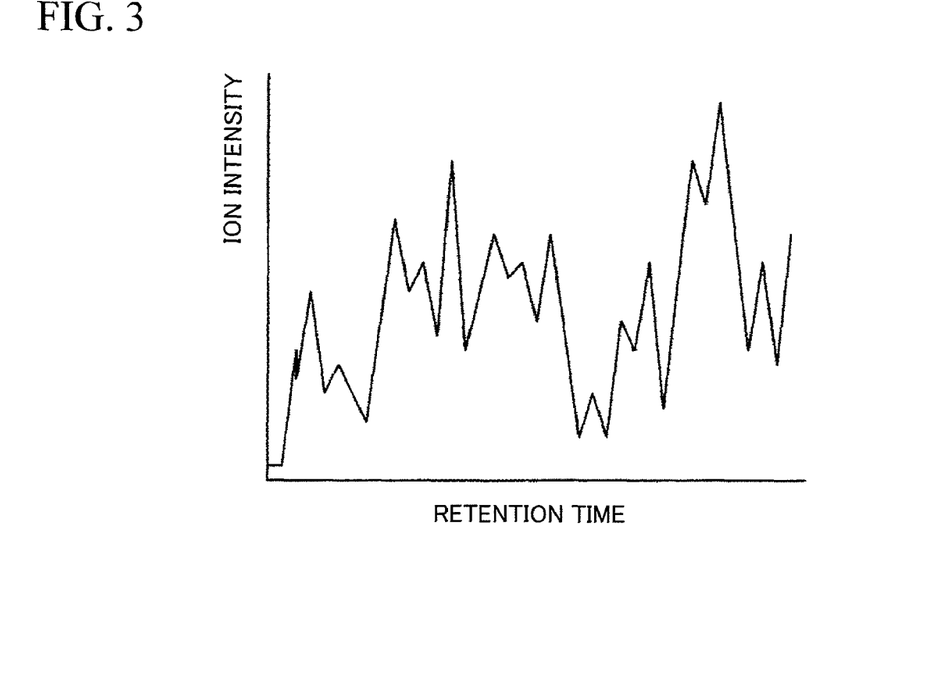
FIG. 3 is a graph showing an example of a total ion chromatogram in the case of subjecting to APCI/MS measurement a separated sample by a first GC.
Figure 4:
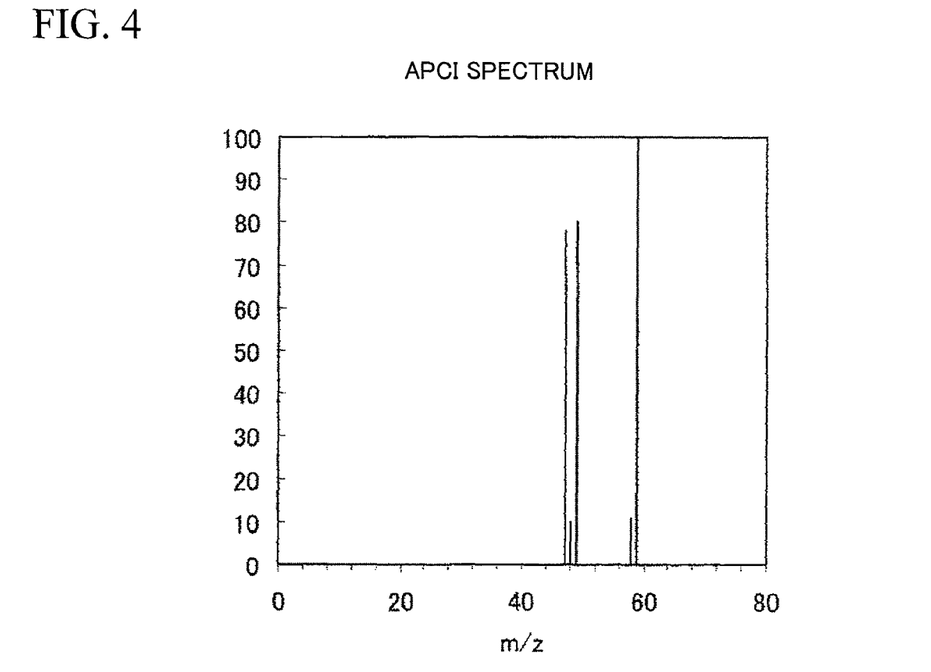
FIG. 4 is a graph showing an APCI spectrum in which three types of substances are measured at the same time.
Figure 5:
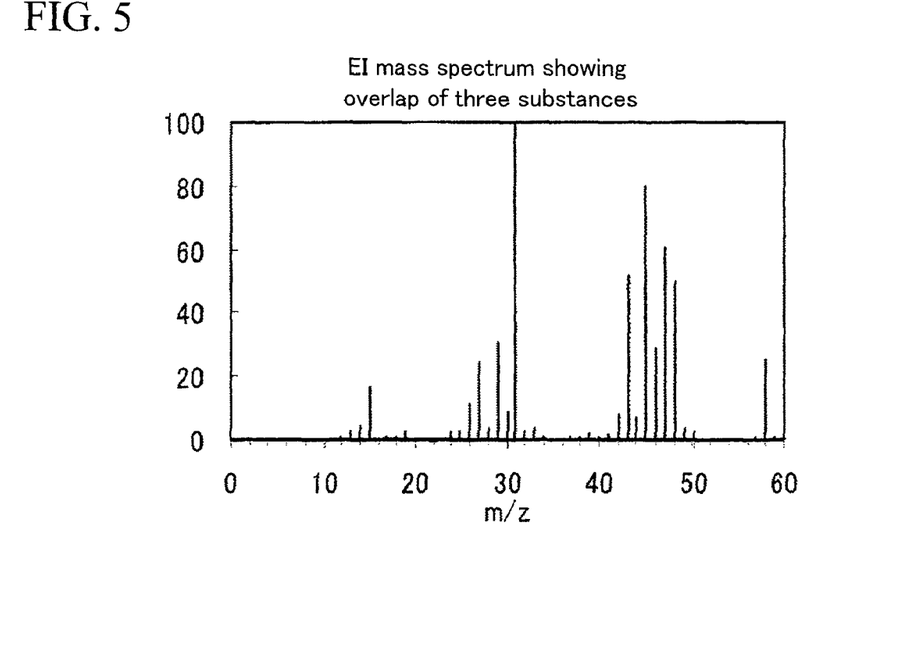
FIG. 5 is a graph showing an example of an EI spectrum in which the three types of substances are measured at the same time.
Figure 6:
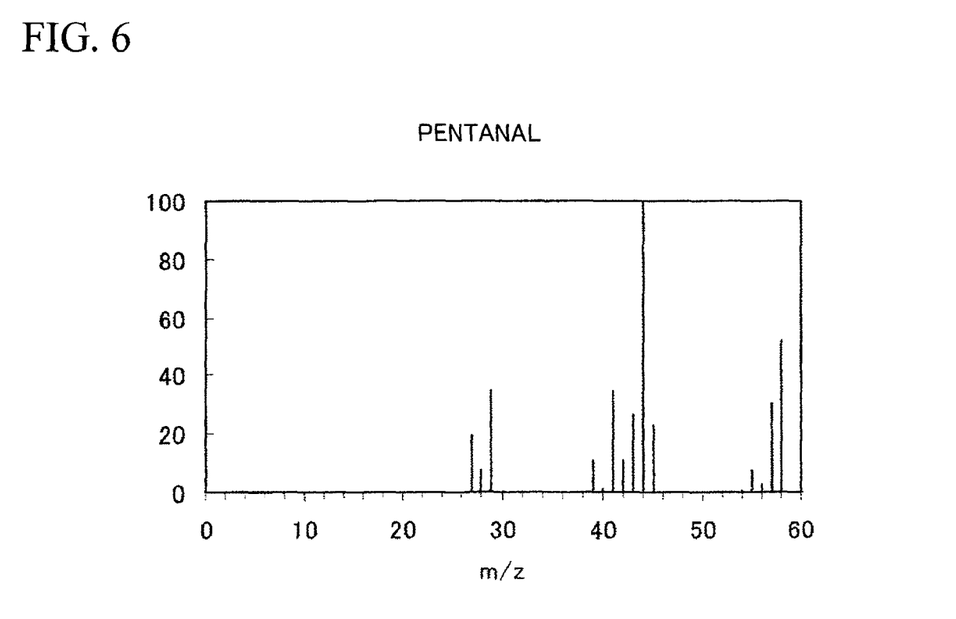
FIG. 6 shows an EI spectrum of pentanal.
Figure 7:
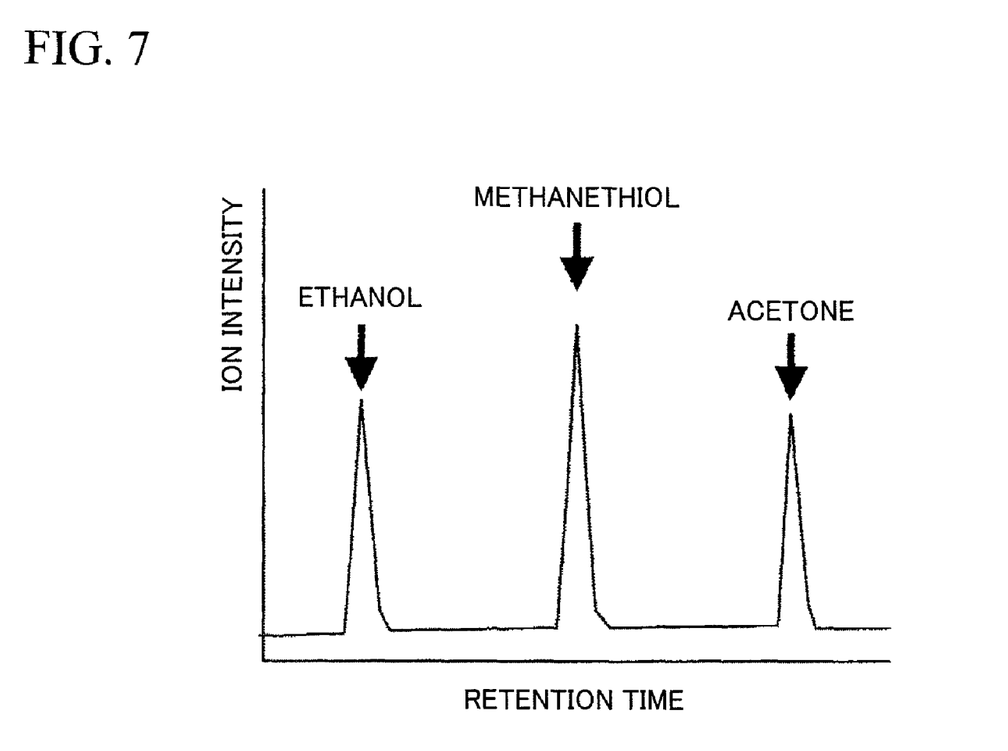
FIG. 7 is a graph showing an example of a chromatogram in the case of separating the three types of substances with a GC configured to increase a temperature at a low rate.

FIG. 3 shows an example of a total ion chromatogram having peaks overlapping each other. FIG. 4 shows an example of an APCI spectrum in which three types of substances are simultaneously observed. This example shows a case of simultaneous detection of a peak being $[M+H]^+$ at m/z 59 concerning acetone (mass number 58), a peak being $[M+H]^+$ at m/z 47 concerning ethanol (mass number 46), and a peak being $[M+H]^+$ at m/z 49 concerning methanethiol. FIG. 5 shows a spectrum to be obtained by introducing the same sample to the EI ion source without making passed through the second GC. Numerous peaks are observed therein as fragment ions generated from the respective substances are detected at the same time. If this spectrum is checked up with a database, this spectrum has a high degree of coincidence with an EI spectrum of pentanal shown in FIG. 6 and is therefore identified as the spectrum of pentanal.

Figure 8:
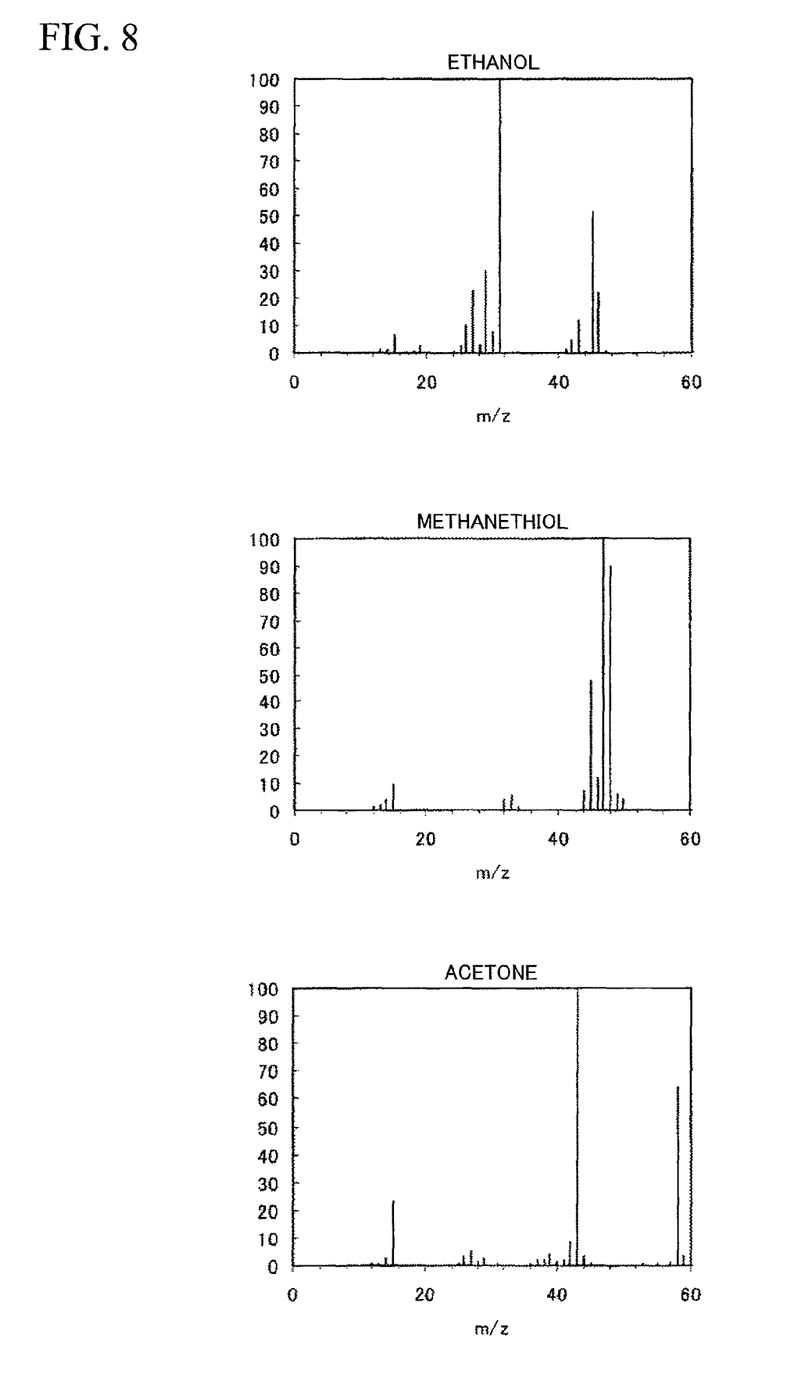
FIG. 8 is a set of graphs showing examples of spectra obtained by subjecting each of the three types of substances to EI measurement.

Accordingly, an EI spectrum as shown in FIG. 8 is obtained when the sample gas in the state of mixing the three ingredients of acetone, ethanol, and methanethiol together is separated by low-speed heating GC and is subjected to EI/MS measurement so as to introduce the respective substances separately to the EI ion source. It is possible to identify the respective substances at high accuracy because only the fragment ions unique to the respective substances are observed therein.

[Second Embodiment]

Figure 9:
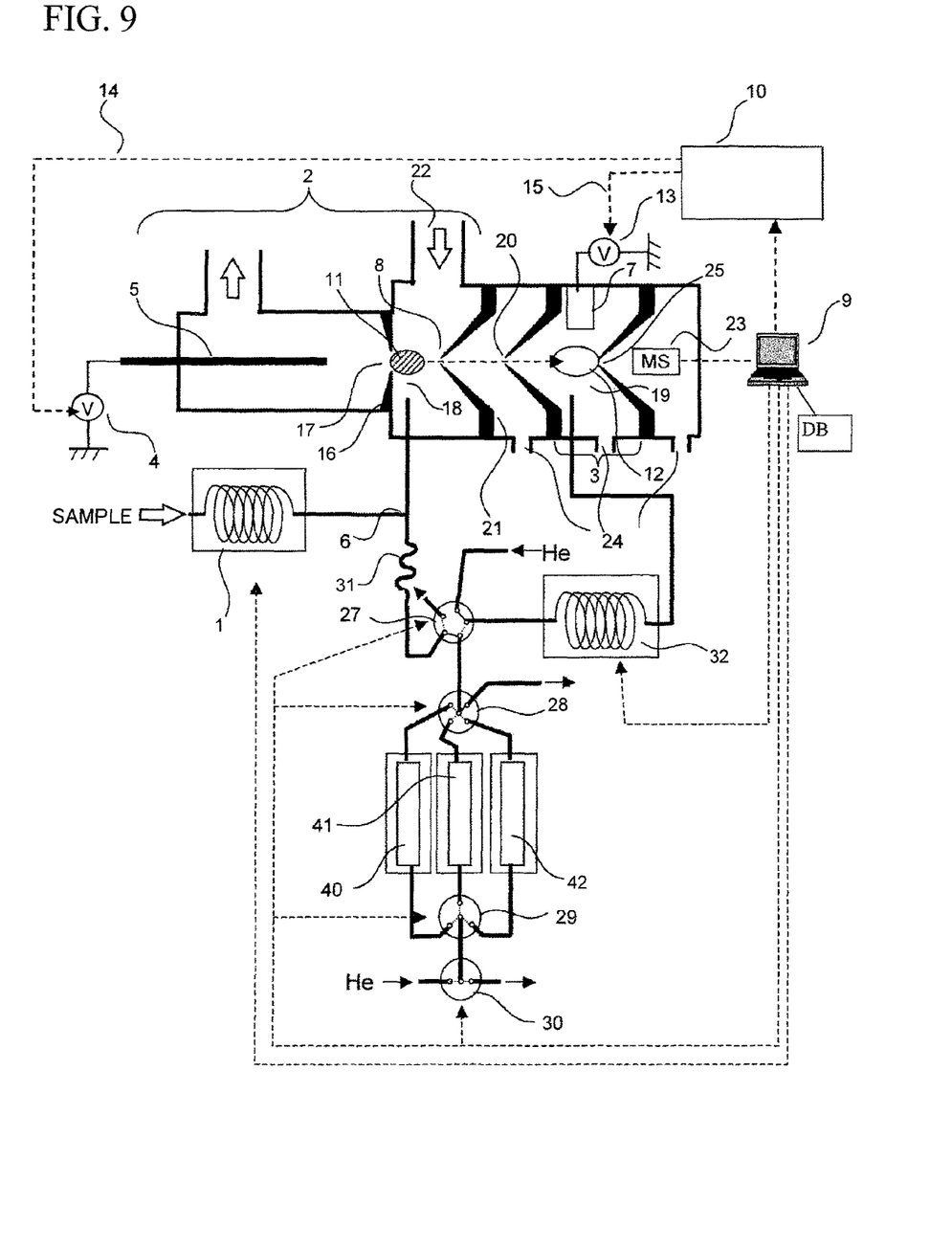
FIG. 9 is a schematic diagram showing another configuration example of the mass spectrometer according to the present invention.

FIG. 9 shows an apparatus configuration example of a mass spectrometry system based on the present invention.

An APCI ion source 2 and an EI ion source 3 are disposed adjacently to each other as the ion sources and a mass spectrometry unit 23 is located on downstream of the EI ion source. A first GC 1 and the second GC 32 are provided in the apparatus. A sample introduced to the first GC 1 is separated in accordance with the column condition, the carrier gas flow rate, and the temperature condition in the first GC 1. The sample gas flowing on the GC column is distributed in two at a tee 6. A part of the separated sample gas is introduced to the APCI ion source 2 and the other part thereof is sent, through the delay channel 31 and a switching valve 27, to a selection valve 28. The selection valve 28 can make selection of either exhausting the sent gas or sending the gas to trap columns.

As similar to the first embodiment, a silica capillary or the like having an inactive inner surface is cut off into an appropriate length for generating a required delay time period and is used as the delay channel 31 provided on the downstream side of the tee 6. In this way, even when the valve is switched after detecting the target substance with the APCI/MS, it is possible to send the sample gas containing the target substance to the trap columns without exhaustion.

Trap columns 40, 41, and 42 each provided with temperature control mechanisms are connected to the selection valve 28, and selection valves 29 and 30 are disposed downstream thereof. The first GC 1, the second GC 2, the valves 27, 28, 29, and 30, and a controller 10 for the ion sources are controlled by the computer 9.

The sample gas that passed through the tee 6, the switching valve 27, and the selection valve 28 further passes through the trap column 40, selection valves 29 and 30, and is then exhausted. In this process, the trap columns are maintained at a low temperature and organic ingredients in the sample gas are captured by the trap columns. When analyzing the sample captured by the trap column by use of the second GC 32, the sample is released by heating the trap column and is sent to the second GC 32 through the selection valve 29, the trap column 40, the selection valve 28, and the switching valve 27 by introducing the carrier gas from the valve 30 to the sample. The same applies to a case of using the trap column 41 or 42.

When multiple trap columns are provided, it is possible to introduce a different sample to each of the trap columns or to use mutually different types of filler thereto. Accordingly, it is possible to use the respective trap columns for different purposes such as using filler having strong retention power for an ingredient having short retention time or using filler having weak retention power for an ingredient having long retention time.

Since the APCI ion source 2 is operable at the atmospheric pressure, it is possible to introduce the sample gas at a gas flow rate around 10 mL/min. Accordingly, the GC column used in the first GC 1 may adopt a wide-bore capillary column having an inside diameter of 0.53 mm, for example. In this way, it is possible to introduce a larger amount of the sample and thereby to detect micro-ingredients therein.

Since the EI ion source 3 is operated at the pressure around $10^{-3}$ torr, it is necessary to introduce the sample gas at a gas flow rate around 1 mL/min. Accordingly, a narrow-bore capillary column having an inside diameter of 0.25 mm, for example, is suitable for the GC column used in the second GC. However, when using the trap columns, a flow rate of introduction of the sample to the trap column may be different from that of the sample, which is released from the trap column, to the second GC 32.

For example, it is possible to set the flow rate of 10 mL/min in the first GC 1 and to set a proportion of the flow rates to be separated to APCI side and the second GC 32 to approximately 1 to 1. In this case, the sample gas is introduced to the trap columns at a flow rate of 5 mL/min. When the trap column is set to a low temperature around $-10°$ C., the sample is condensed on the upstream side of the trap. For this reason, it is possible to maintain separation in the second GC favorably even when the sample is sent to the second GC at the flow rate of 1 mL/min by introducing the carrier gas from the selection valve 30 at the time of heating and releasing the sample from the trap column. By using the trap column as described above, it is possible to introduce a larger amount of the sample to the EI ion source. Particularly in the case of identifying a substance contained only in a very small amount by use of the EI/MS, identification accuracy is improved because ion intensity is enhanced.

Figure 10:
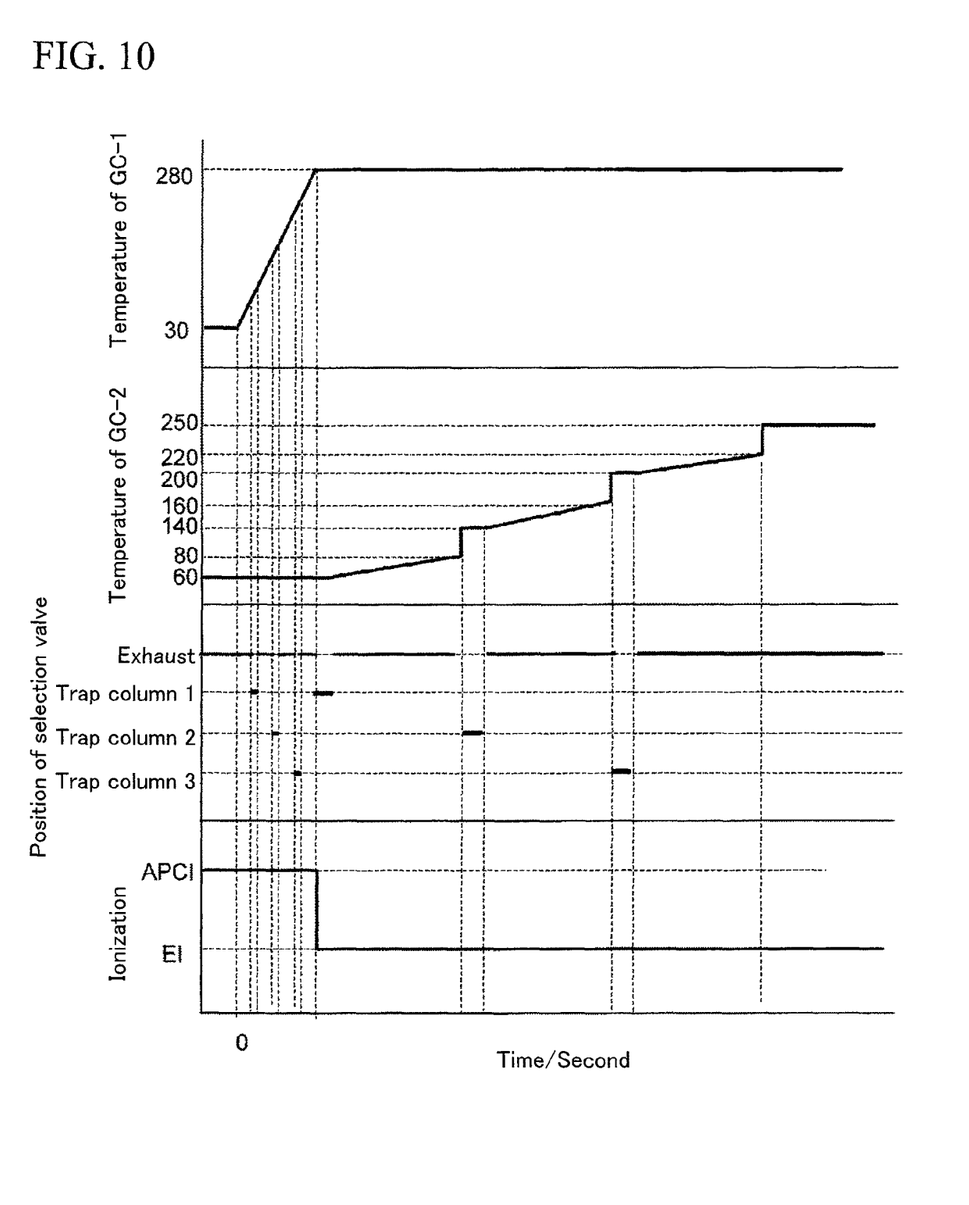
FIG. 10 is a chart showing time control of operations of respective units in measurement using the apparatus configuration shown FIG. 9.

FIG. 10 shows an example of operations of the respective units in measurement using the apparatus configuration in FIG. 9.

Preceding the measurement using the APCI and the EI, multiple specimens are retrieved from a patient and a healthy person and all the specimens are subjected to GC/APCI/MS measurement under the same condition. Peaks unique to the specimen of the patient or the healthy person are selected by means of comparing respective measurement results. These peaks are defined as the disease marker candidates and a list of retention time of the GC and spectra of substances among them which are subject to identification by the EI/MS is recorded on the computer. FIG. 10 shows the case of referring three substances as identification targets by the EI/MS.

It is preferable to configure the first GC to perform separation of the sample under the same condition as the method used for selecting the disease marker candidate. The substance separated by the first GC is detected with the APCI/MS. When the substance is confirmed as a first target disease marker candidate by the computer based on an obtained spectrum pattern and retention time, the selection valves 28 and 29 are switched to positions for a trap 1 to send the sample gas to a trap column 1. In the case of a second or third disease marker candidate, the selection valves 28 and 29 are similarly switched to a trap 2 or a trap 3 to send the sample gas to the trap column 41 or 42. After completion of sending the entire target sample to the trap columns, the substances are sent to the second GC in the order of earlier elution to execute separation and the EI/MS measurement.

It is possible to determine a temperature method for separation in the second GC by use of the temperature of the first GC at the time of elution of the sample. For example, when the first GC and the second GC adopt the GC columns having the same type of a stationary phase, the sample is separated with the first GC by increasing the temperature from 30° C. to 280° C. at 50° C./min. When separating the substance eluted at 70° C. during this period by use of the second GC, the temperature condition of the second GC is set to a temperature increase at 1° C./min from 60° C. to 80° C. When separating the substance eluted at 150° C. by use of the second GC, the temperature condition of the second GC is set to a temperature increase at 1° C./min from 140° C. to 160° C. When separating the substance eluted at 210° C. by use of the second GC, the temperature condition of the second GC is set to a temperature increase at 1° C./min from 200° C. to 220° C. By the above-mentioned procedures stated as examples, it is possible to separate the target substances efficiently by use of the second GC.

What is claimed is:

1. A mass spectrometer comprising:
   a first separator;
   a first sample ion source configured to perform ionization of a sample separated by the first separator;
   a second separator;
   a tee configured to distribute, along diverging channels, the sample separated by the first separator to the first sample ion source and to the second separator;
   a second sample ion source configured to perform ionization of the sample separated by the second separator; and
   only one mass spectrometry unit, configured to detect the sample ionized by the first sample ion source and the sample ionized by the second sample ion source,
   wherein the second sample ion source is located on the downstream side, in a traveling direction of ions, of the first sample ion source, and
   the mass spectrometry unit is located on the downstream side, in the traveling direction of ions, of the second sample ion source.

2. The mass spectrometer according to claim 1, wherein the pressure in the second sample ion source is lower than a pressure in the first sample ion source.

3. The mass spectrometer according to claim 1, wherein the first sample ion source generates a sample ion by atmospheric pressure chemical ionization, and the second sample ion source generates a sample ion by electron impact ionization.

4. The mass spectrometer according to claim 1, further comprising:

a controller configured to control ionization of the sample by the first sample ion source and ionization of the sample by the second sample ionization source, wherein the controller selectively operates the first sample ion source and the second sample ion source.

5. The mass spectrometer according to claim 1, further comprising:

a delay channel located between the tee and the second separator and configured to pass the sample, wherein a time period required for the sample separated by the first separator to pass through the delay channel via the tee is longer than a time period required for the sample separated by the first separator to be ionized by the first sample ion source and to be detected.

6. The mass spectrometer according to claim 5, further comprising:

a mechanism located between the delay channel and the second separator and configured to send the sample separated by the first separator to a trap column;

a device configured to control a temperature of the trap column; and a mechanism configured to send the sample captured by the trap column to the second separator.

7. The mass spectrometer according to claim 6, comprising:

a plurality of the trap columns; and a mechanism configured to introduce different samples to the trap columns.

8. The mass spectrometer according to claim 1, wherein a center of an opening at an end of the first separator is located in a position such that a relation between a flow rate Q of a sample gas flowing through the opening at the end of the first separator and a flow rate Q', out of Q, which is exhausted through an aperture to a mid-differential vacuum pumping region satisfies $0.02Q \leq Q' \leq 0.9Q$.

9. The mass spectrometer according to claim 8, wherein the opening at the end of the first separator is located in a position such that a distance from an axis to the center of the opening at the end of the first separator is not more than twice as long as a radius of the primary ion introduction aperture, the axis connecting a center of a primary ion introduction aperture, through which primary ions passes, to a center of a aperture, through which of the sample ions travel.

10. A method of mass spectrometry comprising the steps of:

distributing, along diverging channels, a sample separated by a first separator to a first sample ion source and to a switching valve, by use of a tee;

ionizing the sample introduced to the first sample ion source by use of the first sample ion source and detecting the ionized sample by use of only one mass spectrometry unit;

switching the sample sent to the switching valve between exhausting and sending to a second separator by use of the switching valve;

further separating the sample by use of the second separator when the sample is sent to the second separator and introducing the sample to a second sample ion source located on a downstream side, in the traveling direction of ions, of the first sample ion source, and detecting the sample ionized by the second sample ion source by use of the mass spectrometry unit.

11. The method of mass spectrometry according to claim 10, wherein a time period required for the sample to reach the switching valve after passing through the tee and a delay channel located between the tee and the second separator is longer than a time period required for the sample to pass through the tee to be ionized by the first sample ion source and then detected by the mass spectrometry unit.

12. The method of mass spectrometry according to claim 10, wherein the sample separated by the first separator is ionized by the first sample ion source and is detected by the mass spectrometry unit, when the sample is confirmed as a target sample candidate based on an obtained spectrum pattern and retention time, the sample separated by the first separator is sent to the second separator by switching the switching valve, and the sample separated by the first separator is further separated by the second separator and is introduced to the second sample ion source.

13. The method of mass spectrometry according to claim 10, wherein the pressure in the second sample ion source is lower than a pressure in the first sample ion source.

14. A method of mass spectrometry comprising the steps of:

distributing, along diverging channels, a sample separated by a first separator to a first sample ion source and to a selection valve, by use of a tee;

ionizing the sample introduced to the first sample ion source by use of the first sample ion source and detecting the ionized sample by use of only one mass spectrometry unit;

switching the selection valve to switch the sample sent to the selection valve between exhausting and sending to a trap column;

capturing the sample in the trap column when the sample is sent to the trap column;

sending the sample captured in the trap column to a second separator;

further separating the sample by use of the second separator and introducing the sample to a second sample ion source; and detecting the sample ionized by the second sample ion source by use of the mass spectrometry unit.

15. The method of mass spectrometry according to claim 14, wherein a time period required for the sample to reach the switching valve after passing through the tee and a delay channel located between the tee and the second separator is longer than a time period required for the sample to pass through the tee to be ionized by the first sample ion source and then detected by the mass spectrometry unit.

16. The method of mass spectrometry according to claim 15, wherein the sample separated by the first separator is ionized by the first sample ion source and is detected by the mass spectrometry unit, when the sample is confirmed as a target sample candidate based on an obtained spectrum pattern and retention time, the sample separated by the first separator is sent to the trap column and is captured in the trap column.

17. The method of mass spectrometry according to claim 14,
wherein a plurality of the trap columns are provided, and a mechanism configured to introduce different samples to the trap columns is provided.

18. The method of mass spectrometry according to claim 14,
wherein the pressure in the second sample ion source is lower than a pressure in the first sample ion source.

19. The mass spectrometer according to claim 1,
wherein the types of mass spectrometry unit applicable thereto include: a quadrupole mass spectrometer, an ion trap mass spectrometer, an ion trap TOF (time of flight) mass spectrometer, and a magnetic sector mass spectrometer.

20. The method of mass spectrometry according to claim 10,
wherein the types of mass spectrometry unit applicable thereto include: a quadrupole mass spectrometer, an ion trap mass spectrometer, an ion trap TOF (time of flight) mass spectrometer, and a magnetic sector mass spectrometer.

21. The method of mass spectrometry according to claim 14,
wherein the types of mass spectrometry unit applicable thereto include: a quadrupole mass spectrometer, an ion trap mass spectrometer, an ion trap TOF (time of flight) mass spectrometer, and a magnetic sector mass spectrometer.

22. The mass spectrometer according to claim 1,
wherein the type of mass spectrometry unit is exclusive of an ion mobility based system.

23. The method of mass spectrometry according to claim 10,
wherein the type of mass spectrometry unit is exclusive of an ion mobility based system.

24. The method of mass spectrometry according to claim 14,
wherein the type of mass spectrometry unit is exclusive of an ion mobility based system.

25. The mass spectrometer according to claim 1,
wherein the tee is configured to distribute, along diverging channels, a distinct portion of the sample separated by the first separator to the first sample ion source and another distinct portion of the sample to the second separator; and
wherein the first sample ion source is configured to perform a different type of ionization than the type of ionization conducted by the second sample ion source.

26. The method of mass spectrometry according to claim 10,
wherein the tee is configured to distribute, along diverging channels, a distinct portion of the sample separated by the first separator to the first sample ion source and another distinct portion of the sample to the second separator; and
wherein the first sample ion source is configured to perform a different type of ionization than the type of ionization conducted by the second sample ion source.

27. The method of mass spectrometry according to claim 14,
wherein the tee is configured to distribute, along diverging channels, a distinct portion of the sample separated by the first separator to the first sample ion source and another distinct portion of the sample to the second separator; and
wherein the first sample ion source is configured to perform a different type of ionization than the type of ionization conducted by the second sample ion source.

* * * * *